United States Patent
Borchert et al.

(10) Patent No.: US 10,131,864 B2
(45) Date of Patent: Nov. 20, 2018

(54) POLYPEPTIDES HAVING PROTEASE ACTIVITY AND POLYNUCLEOTIDES ENCODING SAME

(71) Applicant: Novozymes A/S, Bagsvaerd (DK)

(72) Inventors: Martin Simon Borchert, Hilleroed (DK); Morten Gjermansen, Greve (DK); Peter Rahbek Oestergaard, Virum (DK); Lone Baekgaard, Frederiksberg (DK); Alexander Mauch, Copenhagen (DK); Hans Peter Heldt-Hansen, Virum (DK); Anne Mette Bhatia, Charlottelund (DK); Christina Lund, Bagsvaerd (DK); Miguel Duarte Guilherme Pereira Toscano, Bagsvaerd (DK)

(73) Assignee: Novozyme A/S, Bagsvaerd (DK)

( * ) Notice: Subject to any disclaimer, the term of this patent is extended or adjusted under 35 U.S.C. 154(b) by 121 days.

(21) Appl. No.: 14/784,488

(22) PCT Filed: Apr. 11, 2014

(86) PCT No.: PCT/EP2014/057370
§ 371 (c)(1),
(2) Date: Oct. 14, 2015

(87) PCT Pub. No.: WO2014/170218
PCT Pub. Date: Oct. 23, 2014

(65) Prior Publication Data
US 2016/0053211 A1 Feb. 25, 2016

(30) Foreign Application Priority Data
Apr. 18, 2013 (EP) .................................... 13164263

(51) Int. Cl.
| | |
|---|---|
| C12N 9/52 | (2006.01) |
| C12N 15/57 | (2006.01) |
| C12N 1/20 | (2006.01) |
| C12N 1/15 | (2006.01) |
| C12C 5/00 | (2006.01) |
| C12C 11/00 | (2006.01) |
| C12N 9/50 | (2006.01) |

(52) U.S. Cl.
CPC ............ *C12C 5/004* (2013.01); *C12C 11/003* (2013.01); *C12N 9/50* (2013.01); *C12N 9/52* (2013.01); *C12Y 304/24* (2013.01)

(58) Field of Classification Search
None
See application file for complete search history.

(56) References Cited

U.S. PATENT DOCUMENTS 5,312,748 A 5/1994 Liu et al.

FOREIGN PATENT DOCUMENTS

| EP | 1326957 B1 | 5/2004 |
| WO | 2010094773 A2 | 8/2010 |
| WO | 2012022745 A1 | 2/2012 |

*Primary Examiner* — David Steadman
(74) *Attorney, Agent, or Firm* — Kelly Reynolds

(57) ABSTRACT

The present invention relates to isolated polypeptides having protease activity, and polynucleotides encoding the polypeptides. The invention also relates to nucleic acid constructs, vectors, and host cells comprising the polynucleotides as well as methods of using the polypeptides in beer production.

18 Claims, No Drawings

Specification includes a Sequence Listing.

SEQUENCE LISTING

<160> NUMBER OF SEQ ID NOS: 3

<210> SEQ ID NO 1
<211> LENGTH: 334
<212> TYPE: PRT
<213> ORGANISM: Dactylosporangium variesporum

<400> SEQUENCE: 1

```
Ala Thr Ala Cys Ala Thr Gly Thr Trp Gly Tyr Leu Asp His Asp Gly
1               5                   10                  15

Val Ala Arg Val Ser Pro Asn Ala Lys Val Trp Ala Tyr Asp Asp Asp
                20                  25                  30

Ala Asn Gly Ala Asp Asp Leu Leu Ala Thr Gly Leu Thr Asp Gly Asn
            35                  40                  45

Gly Arg Phe Asn Leu Cys Tyr Asp Asn Thr Asp Asp Glu Gly Gly Gly
        50                  55                  60

Gln Asp Val Tyr Val Arg Thr Ala Thr Glu Asn Thr Leu Trp Ile Ile
65                  70                  75                  80

Arg Asn Gly Arg Thr Arg Lys Ser Tyr Ser Phe Tyr Thr Asp Val Ile
                85                  90                  95

Ala Asn Gly Gly Ser Ala Val Asp Phe Gly Thr Val Arg Pro Ser Asp
            100                 105                 110

Pro Ala Leu Met Arg Gly Val Glu Ala Phe Asp Thr Val Asn Ala Ala
        115                 120                 125

Trp Asn Trp Thr Pro Gly Asn Cys Trp Asp Ala Arg Asp Thr Thr Cys
130                 135                 140

Arg Gln Gly Lys Ile Asn Trp Ala Pro Asp Ser Thr Asp Gly Tyr
145                 150                 155                 160

Tyr Ser Leu Gln Glu Asn Ala Val His Leu Ala Ala Glu Asp Pro Asp
                165                 170                 175

Ser Asn Ile Leu Val Leu His Glu Phe Gly His Tyr Met Met Asp Asp
            180                 185                 190

Val Tyr Glu Asp Asp Phe Pro Pro Ala Pro Asn Cys Ser Pro His Tyr
        195                 200                 205

Ile Thr Lys Ile Ser Ser Ala Gly Cys Ala Trp Thr Glu Gly Phe Ala
210                 215                 220

Thr Trp Phe Gly Val Ala Val Leu Gly Asp Pro Thr Phe Arg Trp Pro
225                 230                 235                 240
```

Gly Gly Arg Thr Leu Asp Leu Glu Gly Pro Thr Trp Gly Thr Ala Asn
            245                 250                 255

Trp Asp Asn Gly Asp Thr Val Glu Gly Arg Val Leu Gly Ser Met Ile
        260                 265                 270

Asp Leu Tyr Asp Thr Thr Asn Glu Pro Gly Asp Thr Cys Ser Glu Asn
            275                 280                 285

Pro Ala Gly Pro Leu Trp Thr Thr Phe Leu Asn His Val Ser Asp Thr
    290                 295                 300

Phe Ala Gln Tyr Trp Ser His Arg Arg Ala Asp Gly Tyr Asp Val Gly
305                 310                 315                 320

Ser Asn Ala Leu Ser Cys Leu Tyr His Asn Thr Ile Asp Tyr
                325                 330

<210> SEQ ID NO 2
<211> LENGTH: 1002
<212> TYPE: DNA
<213> ORGANISM: Artificial sequence
<220> FEATURE:
<223> OTHER INFORMATION: Synthetic gene encoding mature peptide

<400> SEQUENCE: 2

| gcgacggctt | cgccacagg  | cacgtgggga | tacttggatc | acgatggcgt | tgctcgcgta | 60   |
| agcccaaacg | ctaaggtatg | ggcttacgat | gatgatgcta | atggagctga | tgatctttta | 120  |
| gctacaggac | ttacgacgg  | aaatggccgt | ttcaacttat | gttatgacaa | cactgacgac | 180  |
| gaaggcggtg | gtcaagatgt | atatgtacgt | actgcgacgg | aaaacactct | ttggatcatc | 240  |
| cgtaatggtc | gcactcgtaa | atcttactct | ttctatacgg | atgttattgc | aaatggtggc | 300  |
| tcagcggttg | atttcggtac | agtacgtcct | tctgatcctg | cacttatgcg | tggcgtagaa | 360  |
| gctttcgaca | ctgtaaatgc | cgcatggaat | tggacacctg | gaaattgctg | ggatgcacgt | 420  |
| gatacgacat | gtcgtcaagg | caagattaac | tgggctccag | attctactga | tggtacgtat | 480  |
| tacagcttgc | aagagaatgc | tgtacactta | gctgctgaag | acccagatag | caatatcctt | 540  |
| gttttacacg | agttcggtca | ctatatgatg | gacgatgttt | acgaagacga | cttccctcct | 600  |
| gcaccaaatt | gttcaccaca | ttacattact | aagatttctt | ctgcaggttg | cgcttggaca | 660  |
| gaaggtttcg | ctacttggtt | cggagttgca | gttttgggtg | acccgacttt | ccgctggcct | 720  |
| ggaggtcgta | ctcttgactt | agaaggccca | acttggggta | ctgcaaattg | ggacaacggc | 780  |
| gacactgttg | aaggtcgcgt | acttggttca | atgattgatc | tttacgacac | gacaaacgaa | 840  |
| ccaggagata | cttgttctga | aaatccggca | ggacctcttt | ggactacttt | cttgaaccac | 900  |
| gtatctgaca | cattcgcgca | gtattggtca | catcgtcgcg | cagatggata | cgacgtaggt | 960  |
| tctaatgcgt | taagctgcct | ttatcacaac | acaattgatt | ac         |            | 1002 |

<210> SEQ ID NO 3
<211> LENGTH: 1671
<212> TYPE: DNA
<213> ORGANISM: Artificial sequence
<220> FEATURE:
<223> OTHER INFORMATION: Synthetic gene encoding the full length
      protease

<400> SEQUENCE: 3

| atgattcgtc | aagttttacg | cggtgttctt | ccacctacgg | cacttcttgc | tgcgatcctt | 60  |
| actgcagcga | caacggctga | agctgcgcca | gctactgcga | ctgctgaggc | tgcaccggca | 120 |
| gcttgtacac | cgtttgaagg | tactggagaa | tggcagtctt | gcttagatgt | acaagtacgt | 180 |

```
cttgcagacg cacctgcact tggagcagaa actcgcttag acattgatgt tcgtactacg    240
gctactcgtt ctgacgttca gttagacgta tcacttcctg caggccttga atgggtacaa    300
cctccagcag gtcttgatac acgcacggtt acgagcgctg taccacttga ccagggtcgt    360
gctcatcatg ccacaggcac agcacgtgta cttaaagatc gcccacttcg ccttactgga    420
aaagtacgtg cggttgcgga aggcccagcg caaattcagg ttagcgctcg ttctggagta    480
gaaagcgaca aaggatcagc tttcttaact gtaggaactc agcagtcacg tcacggtatt    540
gctgttcaag aagctaatcg cgcagttcgc gtagacgaac gcgctactct tgctcatcca    600
aaatctcctc acaaaccagc tggcgaaact gcaggtgaaa ctgcgggtga aactgctggt    660
gctcttgcga cggcttgcgc cacaggcacg tggggatact tggatcacga tggcgttgct    720
cgcgtaagcc caaacgctaa ggtatgggct tacgatgatg atgctaatgg agctgatgat    780
cttttagcta caggacttac ggacggaaat ggccgtttca acttatgtta tgacaacact    840
gacgacgaag gcggtggtca agatgtatat gtacgtactg cgacggaaaa cactctttgg    900
atcatccgta atggtcgcac tcgtaaatct tactctttct atacggatgt tattgcaaat    960
ggtggctcag cggttgattt cggtacagta cgtccttctg atcctgcact tatgcgtggc   1020
gtagaagctt tcgacactgt aaatgccgca tggaattgga caccctggaaa ttgctgggat   1080 gcacgtgata cgacatgtcg tcaaggcaag attaactggg ctccagattc tactgatggt   1140
acgtattaca gcttgcaaga gaatgctgta cacttagctg ctgaagaccc agatagcaat   1200
atccttgttt tacacgagtt cggtcactat atgatggacg atgtttacga agacgacttc   1260
cctcctgcac caaattgttc accacattac attactaaga tttcttctgc aggttgcgct   1320
tggacagaag gtttcgctac ttggttcgga gttgcagttt tgggtgaccc gactttccgc   1380
tggcctggag gtcgtactct tgacttagaa ggcccaactt ggggtactgc aaattgggac   1440
aacggcgaca ctgttgaagg tcgcgtactt ggttcaatga ttgatcttta cgacacgaca   1500
aacgaaccag gagatacttg ttctgaaaat ccggcaggac ctctttggac tactttcttg   1560
aaccacgtat ctgacacatt cgcgcagtat tggtcacatc gtcgcgcaga tggatacgac   1620
gtaggttcta atgcgttaag ctgcctttat cacaacacaa ttgattacta a            1671
```

POLYPEPTIDES HAVING PROTEASE ACTIVITY AND POLYNUCLEOTIDES ENCODING SAME

CROSS-REFERENCE TO RELATED APPLICATIONS

This application is a 35 U.S.C. 371 national application of PCT/EP2014/057370 filed Apr. 11, 2014, which claims priority or the benefit under 35 U.S.C. 119 of European application no. 13164263.9 filed Apr. 18, 2013 the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having protease activity, and polynucleotides encoding the polypeptides. The invention also relates to nucleic acid constructs, vectors, and host cells comprising the polynucleotides as well as methods of using the polypeptides in beer production.

Description of the Related Art

The present invention provides polypeptides having protease activity and polynucleotides encoding the polypeptides.

The present invention also provides methods of improving colloidal stability in a beverage using the polypeptides of the invention.

Many beverages like beer, wine, juice etc. develop precipitates during manufacture or upon storage. This phenomenon is described as haze formation. One form of haze formation is generally believed to be due to interaction of proteins and polyphenols present in the beverage. This interaction leads to the formation of insoluble or semi-soluble suspension of colloidal particles. Since haze formation may resemble cloudiness produced by microbial contamination, it is generally preferred that the beverages, particularly beer, are very clear and transparent even upon long storage. Hence processes have been developed to reduce such haze formation. These processes target either the proteins or the polyphenols or both.

Silica gels, Bentonite, Poly(VinylPolyPyrrolidone) (PVPP) etc. have been used to adsorb proteins and polyphenols, decreasing haze formation and improving colloidal stability. However, such materials, when used repeatedly result in diminishing returns and consequently lead to increased costs. Moreover, they also remove other desirable compounds from the beverage, which may affect its quality.

Enzymes, particularly proteases, are also used during fermentation to improve the colloidal stability of beverages, particularly beer. Traditionally, proteases like papain and bromelain have been used to reduce chill haze formation. However, these proteases have been shown to affect the foam stability of the beverage by hydrolysing the proteins that are involved in formation and stabilization of foam. Moreover, these also cause flavour changes in the beverage. Another approach has been the use of proteases that hydrolyse mostly the haze forming proteins and rarely the foam forming proteins. For example, a prolyl specific endoprotease is known (e.g., from EP 1326957).

SUMMARY OF THE INVENTION

The present invention relates to polypeptides having protease activity so we claim:

A polypeptide having protease activity, selected from the group consisting of:

(a) a polypeptide having at least 60% sequence identity to the polypeptide of SEQ ID NO: 1;

(b) a polypeptide encoded by a polynucleotide that hybridizes under low stringency conditions with the mature polypeptide coding sequence of SEQ ID NO: 2;

(c) a polypeptide encoded by a polynucleotide having at least 60% sequence identity to the polypeptide coding sequence of SEQ ID NO: 2;

(d) a variant of the polypeptide of SEQ ID NO: 1 comprising a substitution, deletion, and/or insertion at one or more positions; and (e) a fragment of the polypeptide of (a), (b), (c), or (d) that has protease activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to methods of improving colloidal stability in a beverage, for example but not limited to, beer, wort based non alcoholic beverage, wine and juice using the polypeptide(s) of the invention. One way of improving colloidal stability is by preventing or reducing haze.

In one aspect, the invention relates to a method of improving colloidal stability in beer comprising contacting a mash and/or a wort with the polypeptide(s) of the invention during the production of beer.

In another aspect, the invention relates to the use of polypeptide(s) of the invention in brewing.

In one aspect, the contacting is done with the wort. In another aspect, the polypeptide(s) is added to the wort. In another aspect, the contacting is done with the mash. In another aspect, the polypeptide(s) is added to the mash. In one aspect, the contacting is done during fermentation. In another aspect, the polypeptide(s) is added during fermentation. In one aspect, the contacting is done after lautering. In another aspect, the contacting is done during sparging. In one aspect, the contacting is done at a temperature of 20°-80° C. In another aspect, the contacting is done at a temperature of at least 30° C. In another aspect, the contacting is done at a temperature of at least 40° C. In one aspect, the contacting is done at a temperature of at least 50° C. In another aspect, the contacting is done at a temperature of at least 60° C. In another aspect, the contacting is done at a temperature of at least 70° C. In one aspect, the contacting is done at a temperature of at least 75° C.

Definitions

Polypeptides having Protease Activity

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

"The term 'protease' is defined herein as an enzyme that hydrolyses peptide bonds. This definition of protease also applies to the protease-part of the terms 'parent protease' and 'protease variant,' as used herein. The term 'protease' includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web (WWW) at world wide web address chem.qmw.ac.uk/iubmb/enzyme/index.html.

"The proteases of the invention and the proteases for use according to the invention are selected from the group consisting of:

(a) proteases belonging to the EC 3.4.24. enzyme group; and/or (b) proteases of the M5 family;

as described in Gene, 88:87-95 (1990) and in MEROPS protease database, release, 9.6(world wide web address merops.sanger.ac.uk). The database is described in Rawlings, N.D., Barrett, A.J. & Bateman, A. (2012) MEROPS: the database of proteolytic enzymes, their substrates and inhibitors. Nucleic Acids Res 40, D343-D350."

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of protease substrates are casein, such as Azurine-Crosslinked Casein (AZCL-casein). Examples of suitable protease assays are described in the experimental part.

Protease activity: The term "protease activity" means a proteolytic activity (EC 3.4) that catalyzes the hydrolysis of an amide bond or a protein by hydrolysis of the peptide bond that links the amino acids together in a polypeptide chain. Several assays for determining protease activity are available in the art. For purposes of the present invention, protease activity is determined according to the procedure described in the Examples. In one aspect, the polypeptides of the present invention have at least 20%, e.g., at least 40%, at least 50%, at least 60%, at least 70%, at least 80%, at least 90%, at least 95%, or at least 100% of the protease activity of the mature polypeptide of SEQ ID NO: 1.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. As a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has protease activity. In one aspect, a fragment contains at least 85%, at least 90%, at least 95% of the number of amino acids of SEQ ID NO: 1.

High stringency conditions: The term "high stringency conditions" means for probes of at least 100 nucleotides in length, prehybridization and hybridization at 42° C. in 5× SSPE, 0.3% SDS, 200 micrograms/ml sheared and denatured salmon sperm DNA, and 50% formamide, following standard Southern blotting procedures for 12 to 24 hours. The carrier material is finally washed three times—each for 15 minutes using 2× SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Low stringency conditions: The term "low stringency conditions" means for probes of at least 100 nucleotides in length, prehybridization and hybridization at 42° C. in 5× SSPE, 0.3% SDS, 200 micrograms/ml sheared and denatured salmon sperm DNA, and 25% formamide, following standard Southern blotting procedures for 12 to 24 hours. The carrier material is finally washed three times—each for 15 minutes using 2× SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is SEQ ID NO: 1.

Mature polypeptide coding sequence: The term "mature polypeptide coding sequence" means a polynucleotide that encodes a mature polypeptide having protease activity. In one aspect, the mature polypeptide coding sequence is SEQ ID NO: 2.

Medium stringency conditions: The term "medium stringency conditions" means for probes of at least 100 nucleotides in length, prehybridization and hybridization at 42° C. in 5× SSPE, 0.3% SDS, 200 micrograms/ml sheared and denatured salmon sperm DNA, and 35% formamide, following standard Southern blotting procedures for 12 to 24 hours. The carrier material is finally washed three times—each for 15 minutes using 2× SSC, 0.2% SDS at 55° C.

Medium-high stringency conditions: The term "medium-high stringency conditions" means for probes of at least 100 nucleotides in length, prehybridization and hybridization at 42° C. in 5× SSPE, 0.3% SDS, 200 micrograms/ml sheared and denatured salmon sperm DNA, and 35% formamide, following standard Southern blotting procedures for 12 to 24 hours. The carrier material is finally washed three times—each for 15 minutes using 2× SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment–
Total Number of Gaps in Alignment).

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment–Total Number of Gaps in Alignment).

Subsequence: The term "subsequence" means a polynucleotide having one or more (e.g., several) nucleotides absent from the 5' and/or 3' end of a mature polypeptide coding sequence; wherein the subsequence encodes a fragment having protease activity.

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 90% pure, e.g., at least 91% pure, at least 92% pure, at least 93% pure , at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having protease activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding one or more (e.g several) amino acids, e.g. 1-5 amino acids adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the protease activity of the mature polypeptide of SEQ ID NO: 2.

Very high stringency conditions: The term "very high stringency conditions" means for probes of at least 100 nucleotides in length, prehybridization and hybridization at 42° C. in 5× SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2× SSC, 0.2% SDS at 70° C.

Very low stringency conditions: The term "very low stringency conditions" means for probes of at least 100 nucleotides in length, prehybridization and hybridization at 42° C. in 5× SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2× SSC, 0.2% SDS at 45° C.

Beverage: The term beverage as used herein has the conventional meaning in the art and includes, but not limited to, beer, wort based non alcoholic beverage, wine and juice.

Beer: The term "beer" as used herein is intended to cover at least beer prepared from mashes prepared from unmalted cereals as well as all mashes prepared from malted cereals, and all mashes prepared from a mixture of malted and unmalted cereals. The term "beer" also covers beers prepared with adjuncts, and beers with all possible alcohol contents including non-alcoholic beers.

Processing Aid: A "processing aid" is an agent that is used during brewing and/or storage to reduce the haze formation. The processing aids include but are not limited to e.g. silica gel, PVPP, bentonite.

Colloidal stability: Colloidal stability of a beer may be defined as the amount of warm cycles before the colloidal instability measured in EBC units becomes greater than 2. One warm cycle corresponds to approximately 25 days of shelf-life (MEBAK 2.15.2.1, Fociertmethode, Vorausbestimmung der chemisch-physikalischen Stabilitat, Methodensamlung der Mitteleuropaischen Brautechniche Analysekommission (MEBAK), Selbstverlag der MEBAK, Freising Weihenstephan).

Haze: Haze is also referred to as "cloudiness" or "turbidity" or "colloidal instability" in the art and hence can be used interchangeably.

The terms "mash", and "wort" have the conventional meaning in the art.

DETAILED DESCRIPTION OF THE INVENTION

Polypeptides having Protease Activity

In an embodiment, the present invention relates to polypeptides, in particular isolated polypeptides, having a sequence identity to the mature polypeptide of SEQ ID NO: 1 of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the polypeptides differ by up to 10 amino acids, e.g., 1, 2, 3, 4, 5, 6, 7, 8, 9, or 10, from the mature polypeptide of SEQ ID NO: 1. In another aspect, the polypeptide differs by no more than 20 amino acids, e.g., 1, 2, 3, 4, 5, 6, 7, 8, 9, 10, 11, 12, 13, 14, 15, 16, 17, 18, 19 or 20 from the mature polypeptide of SEQ ID NO: 1.

A polypeptide of the present invention preferably comprises or consists of the amino acid sequence of SEQ ID NO: 1 or an allelic variant thereof; or is a fragment thereof having protease activity. In another aspect, the polypeptide comprises or consists of the mature polypeptide of SEQ ID NO: 1. In another embodiment, the present invention relates to an isolated polypeptide having protease activity encoded by a polynucleotide that hybridizes under very low stringency conditions, low stringency conditions, medium stringency conditions, medium-high stringency conditions, high stringency conditions, or very high stringency conditions with the mature polypeptide coding sequence of SEQ ID NO: 2, (Sambrook et al., 1989, *Molecular Cloning, A Laboratory Manual*, 2d edition, Cold Spring Harbor, N.Y.).

The polynucleotide of SEQ ID NO: 2 or a subsequence thereof, as well as the polypeptide of SEQ ID NO: 1 or a fragment thereof, may be used to design nucleic acid probes to identify and clone DNA encoding polypeptides having protease activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 2 or a subsequence thereof, the carrier material is used in a Southern blot.

For purposes of the present invention, hybridization indicates that the polynucleotide hybridizes to a labeled nucleic acid probe corresponding to (i) SEQ ID NO: 2; (ii) the mature polypeptide coding sequence of SEQ ID NO: 2; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to an isolated polypeptide having protease activity encoded by a polynucleotide having a sequence identity to the mature polypeptide coding sequence of SEQ ID NO: 2 of at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 1 comprising a substitution, deletion, and/or insertion at one or more (e.g., several) positions. In an embodiment, the number of amino acid substitutions, deletions and/or insertions introduced into the mature polypeptide of SEQ ID NO: 1 is not more than 20, e.g., 1, 2, 3, 4, 5, 6, 7, 8, 9, 10, 11, 12, 13, 14, 15, 16, 17, 18, or 19. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

We have in Example 6 shown various substitutions that do not alter the haze reduction capacity of the enzyme.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus to a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides having Protease Activity

A polypeptide having protease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. In one aspect, the polypeptide is obtained from Dactylosporangium, such as, but not limited to, Dactylosporangium variesporum (renamed as Saccharothrix variisporea Cf. Kim et al., 2011, Int. J. Syst. Evol. Microbiol., 2011, 61, 310-314).

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).
Polynucleotides The present invention also relates to isolated polynucleotides encoding a polypeptide, of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Dactylosporangium* or *Saccharothrix*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 2, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.
Nucleic Acid Constructs The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli,* and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces.* Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum,*

*Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Dactylosporangium* cell. In another aspect, the cell is a *Dactylosporangium variesporum* cell. In one aspect, the cell is a *Saccharothrix* cell. In another aspect, the cell is a *Saccharothrix variisporea* cell. In another aspect, the cell is *Saccharothrix variisporea* ATCC 31203 or DSM 43911.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for proteases. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification,* Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana.*

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide of the present invention. Preferably, the compositions are enriched in such a polypeptide. The term "enriched" indicates that the protease activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses

The process of beer-brewing is well known to the person skilled in the art. A conventional procedure may be outlined in the following way:

The starting material is malted (i.e. dampened or soaked, germinated and subsequently dried) barley and/or unmalted adjuncts, called the grist. During the mashing, where the grist is ground and mixed with water, heated and stirred, the polymers including carbohydrates are degraded by the aid of the enzymes naturally present in the malt.

After mashing, it is necessary to separate the liquid extract (the wort) from the solids (spent grain particles and adjunct particles) in order to get a clear wort. This process is described as lautering. Prior to lautering, the mash temperature may be raised to about 75-78° C. (known as mashing-off). Wort filtration is important because the solids are enriched in large amounts of protein, poorly modified starch, lipids and fatty acids, silicates, and polyphenols (tannins) and proteins.

The extract retained in the spent grain after collection of the first wort may also be washed out by adding hot water on top of the lauter cake. This process is called sparging. The hot water flows through the spent grain and dissolves the remaining extract. The diluted wort is called second wort and its extract decreases from the original gravity of the first wort down to 1-2%. After addition of hops, the wort is boiled. Hereby numerous substances including several proteins are denatured and a precipitation of protein-polyphenol complexes will take place. After cooling and removal of precipitates, the finished beer wort is aerated and yeast is added. After a main fermentation, lasting typically 5-10 days, most of the yeast is removed and the so-called green beer is stored at a low temperature, typically at 0-5 degrees C. for 1 to 12 weeks. During this period, the remaining yeast will precipitate or sediment together with protein-polyphenol complexes and other insoluble substances. To remove the remaining excess dispersed particles, a filtration is performed. The fermented beer may now be carbonized prior to bottling. Carbon dioxide not only contributes to the perceived "fullness" or "body", it imparts "tingling" and "freshness" too. Moreover, it acts as a flavor enhancer, and as an enhancer of the foaming potential and plays an important role in extending the shelf life of the product.

Without being bound by theory, it is believed that the interaction between proteins and polyphenols in beer stored at low temperatures or for a long time, leads to development of aggregates which are referred to as haze. Since the formation of haze affects one of the quality parameters of beer, i.e., colloidal stability, methods have been developed which prevent such haze formation. During the process of brewing, a majority of the protein-polyphenol complexes precipitate by cooling the liquid during beer maturation. Any remaining polyphenols and/or proteins are removed using PVPP, silica gel, bentonite etc.

Another method of reducing haze formation is by the use of proteases. Proteases like papain, are used to cleave the proteins, possibly yielding lower and/or more soluble protein-polyphenol aggregates. However, the use of these enzymes also affects the proteins involved in foam formation and foam stability, further affecting the quality of the final beer.

The inventors found that contacting a mash and/or a wort with the polypeptide(s) of the present invention during the production of beer leads to improved colloidal stabilization and/or foam stability. The inventors have also surprisingly found that contacting a mash and/or a wort with the polypeptide(s) of the present invention during the production of beer leads to improved colloidal stabilization without substantially affecting foam stability.

A polypeptide(s) to be used according to the invention is preferably purified. The term "purified" as used herein covers enzyme protein preparations where the preparation has been enriched for the enzyme protein in question. Such enrichment could for instance be: the removal of the cells of the organism from which an enzyme protein was produced, the removal of non-protein material by a protein specific precipitation or the use of a chromatographic procedure where the enzyme protein in question is selectively adsorbed and eluted from a chromatographic matrix. The polypeptide(s) may have been purified to an extent so that only minor amounts of other proteins are present. The expression "other proteins" relates in particular to other enzymes. A polypeptide(s) to be used in the method of the invention may be "substantially pure", i.e. substantially free from other components from the organism in which it was produced, which may either be a naturally occurring microorganism or a genetically modified host microorganism for recombinant production of the polypeptide(s).

However, for the uses according to the invention, the polypeptide(s) need not be that pure. It may, e.g., include other enzymes. In a preferred aspect, the polypeptide(s) to be used in the method of the invention has been purified to contain at least 20%, preferably at least 30%, at least 40% or at least 50%, (w/w) of polypeptide(s) out of the total protein.

In one aspect, contacting of the polypeptide(s) is with either a mash or a wort or both. In another aspect, the contacting of the polypeptide(s) is with the mash or with the mashing water or with the grist. In a preferred aspect, the contacting with the mash is during mashing. In one aspect, the contacting with the mash is during mashing-off. In another aspect, the contacting is during lautering. In one aspect, the contacting is during sparging. In another aspect, the contacting is with the wort. In one aspect, the polypeptide(s) is added to the wort. In one aspect, the contacting is after lautering. In another aspect, the contacting is after lautering but before wort boiling. In another aspect, the contacting is after wort boiling but before fermentation. In another preferred aspect, the contacting is during fermentation.

The contacting is done at a temperature depending on the optimum temperature for the enzyme and also the stage at which the enzyme is added. The skilled person would know how to calculate the optimum temperature for the enzyme. For purposes of this invention, the contacting is done generally at the temperature of at least 20° C., e.g., at least 25° C., at least 30° C., at least 35° C., at least 40° C., at least 45° C. at least 50° C., at least 55° C., preferably such as at least 60° C., such as at least 65° C., more preferably such as at least 70° C., and most preferably such as 75-80° C. In particular, the contacting is done at a temperature range of about 20-80° C., e.g. 30-80° C., such as about 40-80° C., preferably such as about 50-80° C.

In one aspect, the contacting is done for a period between 3 min to 5 hours, e.g. between 5 min to 5 hours, preferably between 5 min and 4 hours, more preferably between 5 min to 180 min e.g., between 5 min to 120 min, more preferably between 10 minutes and 120 minutes and most preferably between 30 min and 90 minutes.

The amount of protease used for contacting generally depends on various factors for example but not limited to the type of protease, the activity of the protease etc. For purposes of this invention, the amount of protease used will generally be about 0.01 mg to about 100 mg EP (Enzyme Protein) per liter of the substrate, preferably about 0.05 to about 50 mg EP per liter of the substrate, more preferably about 0.1 to about 40 mg EP per liter of the substrate.

In particular, the amount of enzyme used will generally be about 0.16 mg to about 16 mg EP per litre of the wort, preferably about 0.8 mg to about 8 mg EP per litre of the wort.

In one aspect, using the method of the invention, the colloidal stability is increased by at least 10% e.g. at least 15%, at least 20%, at least 25%, at least 30%, at least 35%, at least 40%, at least 45%, at least 50%, at least 55%, at least 60%, at least 65%, at least 70%, at least 75% such as at least 80%, such as at least 81%, such as at least 82%, such as at least 83%, such as at least 84%, such as at least 85% such as at least 86%, such as at least 87%, such as at least 88%, such as at least 89%, such as at least 90%, such as at least 91%, such as at least 92%, such as at least 93%, such as at least 94%, such as at least 95% such as at least 96%, such as at least 97%, such as at least 98%, such as at least 99%, such as at least 100%, such as at least 101%, such as at least 102%, such as at least 103%, such as at least 104%, such as at least 105% such as at least 106%, such as at least 107%, such as at least 108%, such as at least 109%, such as at least 110% compared to a beer brewed in the absence of the polypeptide(s). In another aspect, the colloidal stability is increased in the range of about 10-110%, e.g. about 20-110%, 30-110%, 40-110%, preferably about 50-110%, more preferably in the range of 60-110%, most preferably in the range of 70-110%, even most preferably in the range of 80-110% compared to a beer brewed in the absence of the polypeptide(s).

Colloidal stability may be determined by use of a method as described in the examples.

In one aspect, the haze is reduced by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, such as at least 80%, such as at least 81%, such as at least 82%, such as at least 83%, such as at least 84%, such as at least 85% such as at least 86%, such as at least 87%, such as at least 88%, such as at least 89%, such as at least 90%, such as at least 91%, such as at least 92%, such as at least 93%, such as at least 94%, such as at least 95% such as at least 96%, such as at least 97%, such as at least 98%, such as at least 99%, such as at least 100% when compared to a beer brewed in the absence of the polypeptide(s). In another aspect, the haze is reduced in the range of about 5-100%, e.g. about 10-100%, 30-100%, 40-100%, preferably about 50-100%, more preferably in the range of 60-100%, most preferably in the range of 70-100%, even most preferably in the range of 80-100% compared to a beer brewed in the absence of the polypeptide(s).

In another aspect, the method of the invention leads to a reduction of haze when compared to a beer processed by using a processing aid.

To quantify the amount of haze in a beverage, a turbidimeter also called a hazemeter is often used. In a turbidimeter the amount of light is measured that is scattered at a pre-described angle relative to the direction of the incident light beam. Turbidity measurements are very suitable for the measurement of haze formed as the result of protein-polyphenol interactions. The haze may be measured, for example, by use of a method as described in the examples.

In another aspect, the method of the invention leads to a decreased use of the processing aids used during brewing and storage to reduce the haze formation. In one aspect, the decrease is 100 percent, meaning no processing agents are used.

In another aspect, the beer is produced without stabilization with silica and preferably without stabilization with silica and PVPP. In one aspect, using the method of the invention, the foam stability is not affected compared to a beer brewed in the absence of the polypeptide(s) of the invention. In one aspect, using the method of the invention, the foam stability is not affected compared to a beer processed using a processing aid.

In one aspect, the foam stability of the beer is at least 80%, e.g., 81%, 82%, 83%, 84%, such as at least 85%, e.g., 86%, 87%, 88%, 89%, such as at least 90%, e.g., 90%, 91%, 92%, 93%, 94%, such as at least 95%, e.g., 96%, 97%, 98%, such as at least 99% compared to a beer brewed in the absence of the polypeptide(s) of the invention. In another aspect, the foam stability of the beer is in the range between 80-99%, e.g., 85-99%, 90-99%, 95-99% compared to a beer brewed in the absence of the polypeptide(s) of the invention.

In another aspect, the foam stability of the beer is at least 80%, e.g., 81%, 82%, 83%, 84%, such as at least 85%, e.g., 86%, 87%, 88%, 89%, such as at least 90%, e.g., 90%, 91%, 92%, 93%, 94%, such as at least 95%, e.g., 96%, 97%, 98%, such as at least 99% compared to a beer brewed in the absence of processing aids. In another aspect, the foam stability of the beer is in the range between 80-99%, e.g., 85-99%, 90-99%, 95-99% compared to a beer brewed in the absence of processing aids.

Foam stability may be determined by use of a method as described in the examples.

In one aspect, the invention relates to the use of polypeptide(s) of the invention in brewing, particularly brewing of beer. In another aspect, the invention relates to a process employing polypeptide(s) of the invention in brewing, particularly brewing of beer. In another aspect, the invention relates to a brewing process employing polypeptide(s) of the invention.

The present invention is further described by the following examples that should not be construed as limiting the scope of the invention.

EXAMPLES

Example 1

Cloning and Expression of a M5 Protease from *Dactylosporangium variesporum* JCM 3273 in *B. subtilis*

*Dactylosporangium variesporum* (strain JCM 3273) has recently been re-classified as *Saccharothrix variisporea* (Kim et al., Int J Syst Evol Microbiol. 2011 February; 61(Pt 2):310-4).

The M5 protease gene originates from the strain number JCM 3273 (Japan Collection of Microorganisms).

A synthetic gene based on the protein sequence of M5 protease from *D. variesporum* was designed with the sequence of SEQ ID NO: 3. (SEQ ID NO:3 encodes the full length protease with signal peptide, pro peptide, and mature protease peptide).

The natural signal peptide was replaced by fusing the synthetic gene to DNA encoding the signal peptide from the alkaline protease from *Bacillus clausii* (aprH) as described in WO 99/43835. The resulting gene was integrated by homologous recombination into the *Bacillus subtilis* host cell genome upon transformation.

The *B. subtilis* expression host was deficient of the following gene products by gene insertion or gene deletion on its chromosome: SpoIIAC-, BioI-, NprE-, AprE-, AmyE-, SrfAC-. The gene construct was expressed under the control of a triple promoter system (as described in WO 99/43835). The gene coding for chloramphenicol acetyltransferase was used as marker (as described in Diderichsen et al., 1993, Plasmid 30: 312-315).

One expression clone was selected and was cultivated on a rotary shaking table in 500 mL baffled Erlenmeyer flasks, each containing 100 mL casein based media supplemented with 34 mg/L chloramphenicol. The clone was cultivated for 3 days at 37° C. and successful expression was determined by SDS-PAGE analysis.

Example 2

Characterization & Purification of M5 Protease

1) Protazyme AK Assay:
Substrate: Protazyme AK tablet (cross-linked and dyed casein; from Megazyme)
Temperature: controlled (assay temperature).
Assay buffers: 100 mM succinic acid, 100 mM HEPES, 100 mM CHES, 100 mM CABS, 1 mM CaCl2, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.
A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 30 minutes on the Eppendorf thermomixer at its highest shaking rate (1400 rpm). The incubation was stopped by transferring the tube back to the ice bath. Then the tube was centrifuged in an ice cold centrifuge for a few minutes and 200 µl supernatant was transferred to a microtiter plate. OD650 was read as a measure of protease activity. A buffer blind was included in the assay (instead of enzyme).

Purification of the M5 Protease from *Dactylosporangium variesporum*

The culture broth from Example 1 was centrifuged (26000×g, 20 min) and the supernatant was carefully decanted from the precipitate. The supernatant was filtered through a Nalgene 0.2 µm filtration unit in order to remove the rest of the *Bacillus* host cells. The 0.2 µm filtrate was transferred to 100 mM H3BO3, 10 mM MES, 2 mM CaCl2, pH 6 on a G25 sephadex column (from GE Healthcare). The G25 sephadex transferred enzyme was applied to a Bacitracin agarose column (from Upfront chromatography) equilibrated in 100 mM H3BO3, 10 mM MES, 2 mM CaCl2, pH 6. After washing the column extensively with the equilibration buffer, the M5 protease was eluted with 100 mM H3BO3, 10 mM MES, 2 mM CaCl2, 1M NaCl, pH 6 with 25% (v/v) 2-propanol. The elution peak was transferred to 50 mM H3BO3, 5 mM MES, 1 mM CaCl2, pH 8.5 on a G25 sephadex column. The G25 sephadex transferred Bacitracin peak was applied to a SOURCE 30Q column (from GE Healthcare) equilibrated in 50 mM H3BO3, 5 mM MES, 1 mM CaCl2, pH 8.5. After washing the column with the equilibration buffer, the M5 protease was eluted with a linear NaCl gradient (0→0.5M) in the same buffer over five column volumes. Fractions from the column were analysed for protease activity (using the Protazyme AK assay at pH 7) and peak-fractions were pooled. The pH of the pool was adjusted to pH 6.0 with 20% CH3COOH. The pH adjusted pool was the purified preparation and was used for further characterization. When the purified preparation was analysed by SDS-PAGE the coomassie stained gel showed a single band.

Characterization of the M5 Protease from *Dactylosporangium variesporum*

The Protazyme AK assay was used for obtaining the pH-activity profile and the pH-stability profile (residual activity after 2 hours at indicated pH-values). For the pH-stability profile the protease was diluted 7× in the different assay buffers to reach the pH-values of these buffers and then incubated for 2 hours at 37° C. After incubation, the pH of the protease incubations was adjusted to the same pH-value by dilution in the pH 7.0 assay buffer. Residual activities were measured at pH 7.0 relative to a sample, which was kept at stable conditions (5° C., pH 7.0). The Protazyme AK assay was used for obtaining the temperature-activity profile at pH 7.0. The results are shown in tables 1-3.

TABLE 1 pH-activity profile at 37° C.

| pH | M5 protease from *Dactylosporangium variesporum* |
|---|---|
| 2 | 0.00 |
| 3 | 0.00 |

TABLE 1-continued pH-activity profile at 37° C.

| pH | M5 protease from *Dactylosporangium variesporum* |
|---|---|
| 4 | 0.00 |
| 5 | 0.01 |
| 6 | 0.28 |
| 7 | 0.98 |
| 8 | 1.00 |
| 9 | 0.61 |
| 10 | 0.03 |
| 11 | 0.02 |

Note:
activities are relative to the optimal pH for the enzyme.

TABLE 2 pH-stability profile (residual activity after 2 hours at 37° C.)

| pH | M5 protease from *Dactylosporangium variesporum* |
|---|---|
| 2 | 0.02 |
| 3 | 0.01 |
| 4 | 0.01 |
| 5 | 0.86 |
| 6 | 0.93 |
| 7 | 0.99 |
| 8 | 0.93 |
| 9 | 0.92 |
| 10 | 0.19 |
| 11 | 0.00 |
| After 2 hours at 5° C. | 1.00 (at pH 7) |

Note:
activities are residual activities relative to a sample, which was kept at stable conditions (5° C., pH 7.0).

TABLE 3

Temperature activity profile at pH 7.0

| Temp (° C.) | M5 protease from *Dactylosporangium variesporum* |
|---|---|
| 15 | 0.00 |
| 25 | 0.01 |
| 37 | 0.07 |
| 50 | 0.46 |
| 60 | 1.00 |
| 70 | 0.46 |
| 80 | 0.07 |

Note:
activities are relative to the optimal temperature for the enzyme.

Other assays in the lab on the M5 protease from *Dactylosporangium variesporum* showed that it was inhibited by 1,10-phenanthroline and EDTA.

The N-terminal sequencing by EDMAN degradation revealed it to be ATACATG.

The relative molecular weight as determined by SDS-PAGE was approx. Mr=37 kDa, and the molecular weight determined by Intact molecular weight analysis was 36658.5Da.

The mature sequence (from MS data, EDMAN degradation data and DNA sequence) is shown in SEQ ID No: 1.

The calculated molecular weight from this mature sequence was 36658.4Da.

Example 3

Role of M5 Protease in Wort Haze Reduction

The M5 protease of Seq ID No: 1 was used in this example.

A standard malt wort was made: 50.0 g grinded malt (0.2 mm) was added to a mashing beaker together with 200 ml H$_2$O (50° C.) and 3.0 ml CaCl$_2$ solution (11.0 g CaCl$_2$.2H$_2$O/500 ml H$_2$O). The following mashing profile was used: 50° C. for 20 min, 63° C. for 30 min, 72° C. for 20 min, 78° C. for 15 min, cooling to 20° C. (1° C. heating/min).

After mashing, additional water was added up to 300 g and the wort was filtered through a Whatman filter 597½. Thereafter one aliquot of the wort was adjusted to pH 6.0 or pH 7.0, pre-heated to 60° C. and incubated with M5 protease in an amount corresponding to 3.2 and 15 mg EP (Enzyme Protein)/Litre wort for 1 hour at 60° C. The control was also kept for 1 hour at 60° C. (pH 6.0 or 7.0) without enzyme treatment.

After the enzyme treatment, the wort was boiled for 15 min and thereafter cooled to 15° C.

The haze in wort was measured by a modified method according to the method published by Siebert 1997 (J. Am. Soc. Brew. Chem. 55(2):73-78, 1997).

In brief, 25 mL wort was transferred to a 25 mL haze meter cell, added 15 mL acetate buffer pH 4.5, stirred for 1 min at 300 rpm and EBC haze units measured (zero value). The haze meter cell was placed on the multipoint stirrer (300 RPM) and added 0.47 mL×2 Brewtan C solution (200 mg tannic acid/1 L) to the wort solution. The haze EBC value was measured on a 2100 AN Turbidimeter after 40 minutes incubation. The background value was then subtracted from the measurement after 40 minutes to give a measure of the potential of forming haze in wort. The results are given in the Table 4.

TABLE 4

Results of wort haze measurements

| | Enzyme incubation conditions | | | Wort haze |
|---|---|---|---|---|
| | Enzyme dosage (mg EP/L wort) | Temp. (° C.) | pH | (EBC units) |
| Control (no enzyme) | 0 | 60 | 6.0 | 14.45 |
| M5 protease | 3.2 | 60 | 6.0 | 8.42 |
| M5 protease | 15 | 60 | 6.0 | 9.21 |
| Control (no enzyme) | 0 | 60 | 7.0 | 13.90 |
| M5 protease | 3.2 | 60 | 7.0 | 8.07 |

From the above table, it is evident that M5 protease can reduce wort haze up to 42% compared to an untreated control at 60° C. pH 6.0 and 7.0 respectively.

The protein degradation pattern of M5 protease for the above conditions demonstrated no Protein Z, LTP1 or BDAI-1 degradation indicating no harm on important foam proteins. Furthermore, the SDS-PAGE result also indicated no degradation of the low molecular weight (LMW) area (10-15 kDa) which is believed to contain foam active proteins.

Example 4

Laboratory Fermentation Trials of M5 Protease Treated Wort

A standard malt wort was produced as described in Example 3.

Wort-pH was adjusted to 6.0 before heating the wort to incubation temperature of 60° C. M5 protease was added to reach a concentration of 3.2 mg EP/Liter wort of and incubated for 1 h. Wort samples were then cooled down to 20° C. and the wort pH adjusted to 5.3 using lactic acid. Hops were added into the wort, before boiling it, for 40 min to reach a calculated bitterness in beer of 15 EBC bitter units.

Boiled wort was centrifuged to remove hot trub. Propagated yeast was added into wort to reach a concentration of 2×10$^7$ cells/mL of wort. Fermentation was conducted in 1 L Pyrex bottles with a lid loosely attached for 7 days at 12° C. Up to day 5, the fermentation broth was shaked at 145 rpm on an orbital shaker. From day 5 to 7, the speed was reduced to 120 rpm. After fermentation the samples were stored on ice for 5 days.

Haze measurement in beer was conducted as described in Example 3.

Foam stability in beer was determined using the following procedure:

In a first step, yeast and remaining coarse precipitates were removed by filtration of the turbid sample through a Whatman 597$^{1/2}$ paper filter into defatted glassware. Aliquots of 250 mL filtrate were transferred into cleaned and defatted bottles (0.5 L) and tempered to 20.0° C. The beer was carbonated to 5.75 g CO$_2$/L by intervallic shaking and resting under constant CO$_2$-pressure and temperature. Foam stability was determined using the standard NIBEM-T foam analyser (Pentair-Norit Haffmans, Venlo, NL) which is capable to correct for temperature deviations. In brief, a volume of beer is foamed up into a standardised glass beaker by a special foam flasher. The glass is transferred into a measurement unit containing a moveable electrode-system which follows the collapsing foam in the glass based on conductivity measurements. The instrument records the time versus the distance of foam collapse. Foam stability is given as the time [in s] until the foam has collapsed by 30 mm in vertical distance (NIBEM 30-value).

TABLE 5

Effect of wort treatment with M5 protease on beer haze and beer-foam stability

| | Enzyme dosage (mg EP/L wort) | Temp. (degrees Celsius) | pH | Beer haze (EBC units) | Foam stability NIBEM 30 (s) | Foam stability (% of control) |
|---|---|---|---|---|---|---|
| Control (no enzyme) | 0 | 60 | 6 | 13.26 +/− 2.52 | 217 ± 28 | 100 |
| M5 protease | 3.2 | 60 | 6 | 3.41 +/− 0.16 | 205 ± 25 | 95 +/− 1. |

Example 5

0.5 L Lab. Fermentation with M5 Protease Added in Fermentation

A standard malt wort was produced as described in Example 3.

Wort samples were then cooled down to 20° C. and the wort pH adjusted to 5.3 using lactic acid. Hops were added into the wort before boiling it for 40 min to reach a calculated bitterness in beer of 15 EBC bitter units. Boiled wort was centrifuged to remove hot trub. M5 protease was added together with pitching the yeast in a concentration of 3.2 mg EP/Liter wort.

Propagated yeast was added into wort to reach a concentration of $2\times10^7$ cells/mL of wort. Fermentation was conducted in 1 L Pyrex bottles with a lid loosely attached for 7 days at 12° C. Up to day 5, the fermentation broth was shaked at 145 rpm on an orbital shaker. From day 5 to 7, the speed was reduced to 120 rpm. After fermentation the samples were stored on ice for 5 days.

Haze measurement in beer was conducted as described in Example 3.

Foam stability in beer was determined using the following procedure:

In a first step, yeast and remaining coarse precipitates were removed by filtration of the turbid sample through a Whatman 597½ paper filter into defatted glassware. Aliquots of 250 mL filtrate were transferred into cleaned and defatted bottles (0.5 L) and tempered to 20.0° C. The beer was carbonated to 5.75 g $CO_2$/L by intervallic shaking and resting under constant $CO_2$-pressure and temperature. Foam stability was determined using the standard NIBEM-T foam analyser (Pentair-Norit Haffmans, Venlo, NL) which is capable to correct for temperature deviations. In brief, a volume of beer is foamed up into a standardised glass beaker by a special foam flasher. The glass is transferred into a measurement unit containing a moveable electrode-system which follows the collapsing foam in the glass based on conductivity measurements. The instrument records the time versus the distance of foam collapse. Foam stability is given as the time [in s] until the foam has collapsed by 30 mm in vertical distance (NIBEM 30-value).

TABLE 6

Effect of M5 protease added in fermentation on beer haze and beer-foam stability

| | Enzyme dosage (mg EP/L wort) | Beer haze (EBC units) | Beer foam (seconds) | Beer foam (% of control) |
|---|---|---|---|---|
| Control (no enzyme) | 0 | 12.57 | 221 | 100 |
| M5 protease | 3.2 | 2.88 | 220 | 100 |

Example 6

M5 Protease Variants Tested in Haze Reduction

Construction of Variants by Site-directed Mutagenesis

Site-directed variants were constructed from the M5 protease (SEQ ID NO:1) comprising specific substitutions according to the invention. The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were synthesized corresponding to the DNA sequence flanking the desired site(s) of mutation, separated by the DNA base pairs defining the insertions/deletions/substitutions. In this manner, the variants listed in Table 7 below were constructed and produced.

In order to test M5 protease variants of the invention, the mutated DNA comprising a variant of the invention was transformed into a competent *B. subtilis* strain and fermented using standard protocols (PS-1 media, 3-4 days, 37° C.).

TABLE 7

Variants of M5

| Code | Mutations |
|---|---|
| M5-002 | G83A |
| M5-003 | S88P |
| M5-005 | G100S |
| M5-007 | M116Q |
| M5-011 | G216S |
| M5-015 | N299R |
| M5-017 | G320S |
| M5-021 | R84V |
| M5-023 | A1P |
| M5-027 | A36P |
| M5-042 | V95P |
| M5-044 | S101P |
| M5-060 | G147P |
| M5-071 | A224P |
| M5-078 | T244P |
| M5-101 | N98S |
| M5-103 | N130S |
| M5-112 | N322S |
| M5-113 | E74K |
| M5-123 | R50E |
| M5-131 | R109E |
| M5-136 | R243Q |
| M5-142 | T2P |
| M5-148 | A215P |

Haze Reduction Experiments

The above mentioned M5 protease variants were tested in haze reduction experiments.

A standard malt (the same as in Example 3) was used for experiment 1. For experiment 2 and experiment 3, 25% wheat (w/w) was included in the mashing.

For the wheat inclusion, the following mashing profile was used: 54° C. for 20 min, 64° C. for 60 min, 72° C. for 20 min, and 80° C. for 5 min. At the beginning of the mashing CEREMIX® Plus MG, a blend of enzymes, and ULTRAFLO® Max, a beer filtration enzyme solution, was added according to the supplier's recommendations.

Incubation conditions for the M5 protease variants were: pH 5.3, temp 60° C., 30 min and enzyme dosage 3.2 mg EP/l.

The results are shown in Table 8.

Table 8 shows that all the tested M5 protease variants (24) have wort haze reduction capacity.

TABLE 8

Haze reduction experiments

| Experiment | M5 variant | Mutations | Wort haze (EBC units) |
|---|---|---|---|
| 1 | Control (no enzyme) | | 12.7 |
| | M5 | — | 6.3 |
| | M5-005 | G100S | 5.4 |
| | M5-007 | M116Q | 6 |
| | M5-011 | G216S | 9 |
| | M5-015 | N299R | 5.9 |
| | M5-017 | G320S | 5.2 |

TABLE 8-continued

Haze reduction experiments

| Experiment | M5 variant | Mutations | Wort haze (EBC units) |
|---|---|---|---|
| | M5-021 | R84V | 5.4 |
| | M5-044 | S101P | 5.5 |
| | M5-060 | G147P | 5.7 |
| | M5-071 | A224P | 8.1 |
| | M5-078 | T244P | 7.4 |
| | M5-101 | N98S | 5.5 |
| | M5-103 | N130S | 6.3 |
| | M5-112 | N322S | 5 |
| | M5-113 | E74K | 5 |
| | M5-131 | R109E | 5.2 |
| 2 | Control (no enzyme) | | 23.1 |
| | M5 | — | 11.8 |
| | M5-002 | G83A | 7.4 |
| | M5-003 | S88P | 6.2 |
| | M5-023 | A1P | 9.0 |
| | M5-027 | A36P | 6.0 |
| | M5-042 | V95P | 8.1 |
| | M5-123 | R50E | 6.1 |
| | M5-136 | R243Q | 6.2 |
| 3 | Control (no enzyme) | | 20.7 |
| | M5 | — | 8.4 |
| | M5-142 | T2P | 8.1 |
| | M5-148 | A215P | 8 |

The invention claimed is:

1. A nucleic acid construct or expression vector comprising a polynucleotide encoding a polypeptide having protease activity, wherein the polynucleotide is operably linked to one or more heterologous control sequences that direct the production of the polypeptide in an expression host, and wherein the polypeptide having protease activity comprises an amino acid sequence having at least 85% sequence identity to the amino acid sequence of SEQ ID NO: 1.

2. An isolated recombinant host cell transformed with the nucleic acid construct or expression vector of claim 1.

3. A method of producing a polypeptide having protease activity, comprising cultivating the isolated recombinant host cell of claim 2, under conditions conducive for production of the polypeptide.

4. The nucleic acid construct or expression vector of claim 1, wherein the polypeptide having protease activity comprises an amino acid sequence that has at least 90% sequence identity to the amino acid sequence of SEQ ID NO: 1.

5. The nucleic acid construct or expression vector of claim 1, wherein the polypeptide having protease activity comprises an amino acid sequence that has at least 95% sequence identity to the amino acid sequence of SEQ ID NO: 1.

6. The nucleic acid construct or expression vector of claim 1, wherein the polypeptide having protease activity comprises an amino acid sequence that has at least 99% sequence identity to the amino acid sequence of SEQ ID NO: 1.

7. The nucleic acid construct or expression vector of claim 1, wherein the polypeptide having protease activity is encoded by a polynucleotide comprising a nucleotide sequence having at least 90% sequence identity to the nucleotide sequence of SEQ ID NO: 2.

8. The nucleic acid construct or expression vector of claim 1, wherein the polypeptide having protease activity is encoded by a polynucleotide comprising a nucleotide sequence having at least 95% sequence identity to the nucleotide sequence of SEQ ID NO: 2.

9. The nucleic acid construct or expression vector of claim 1, wherein the polypeptide having protease activity is encoded by a polynucleotide comprising a nucleotide sequence having at least 99% sequence identity to the nucleotide sequence of SEQ ID NO: 2.

10. The nucleic acid construct or expression vector of claim 1, wherein the polypeptide having protease activity comprises the amino acid sequence of SEQ ID NO: 1.

11. An isolated recombinant host cell transformed with the nucleic acid construct or expression vector of claim 4.

12. An isolated recombinant host cell transformed with the nucleic acid construct or expression vector of claim 5.

13. An isolated recombinant host cell transformed with the nucleic acid construct or expression vector of claim 6.

14. An isolated recombinant host cell transformed with the nucleic acid construct or expression vector of claim 10.

15. A method of producing a polypeptide having protease activity, comprising cultivating the isolated recombinant host cell of claim 11, under conditions conducive for production of the polypeptide.

16. A method of producing a polypeptide having protease activity, comprising cultivating the isolated recombinant host cell of claim 12, under conditions conducive for production of the polypeptide.

17. A method of producing a polypeptide having protease activity, comprising cultivating the isolated recombinant host cell of claim 13, under conditions conducive for production of the polypeptide.

18. A method of producing a polypeptide having protease activity, comprising cultivating the isolated recombinant host cell of claim 14, under conditions conducive for production of the polypeptide.

* * * * *